US012653729B2

(12) United States Patent
Cecchetto

(10) Patent No.: US 12,653,729 B2
(45) Date of Patent: Jun. 16, 2026

(54) ABSORBENT ARTICLE WITH IMPROVED LAMINATE TOPSHEET

(71) Applicant: The Procter & Gamble Company, Cincinnati, OH (US)

(72) Inventor: Pietro Cecchetto, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 324 days.

(21) Appl. No.: 18/330,682

(22) Filed: Jun. 7, 2023

(65) Prior Publication Data

US 2023/0390125 A1     Dec. 7, 2023

Related U.S. Application Data

(60) Provisional application No. 63/348,594, filed on Jun. 3, 2022.

(51) Int. Cl.
*A61F 13/512*       (2006.01)
*A61F 13/15*        (2006.01)
            (Continued)

(52) U.S. Cl.
CPC ...... *A61F 13/5123* (2013.01); *A61F 13/5121* (2013.01); *A61L 15/24* (2013.01);
            (Continued)

(58) Field of Classification Search
CPC .............. A61F 13/5123; A61F 13/5121; A61F 2013/15406; A61F 2013/51147; A61F 2013/51165; A61F 13/51121
See application file for complete search history.

(56) References Cited

U.S. PATENT DOCUMENTS 3,967,623  A     7/1976  Butterworth
4,041,951  A     8/1977  Sanford
            (Continued)

FOREIGN PATENT DOCUMENTS

CN       1875899  A     12/2006
CN       1942520  A     4/2007
            (Continued)

OTHER PUBLICATIONS

All Office Actions; U.S. Appl. No. 18/811,116, filed Aug. 21, 2024.
            (Continued)

*Primary Examiner* — Jessica Arble
(74) *Attorney, Agent, or Firm* — Sarah M. DeCristofaro

(57) ABSTRACT

An absorbent article having a topsheet of particular configuration and composition is disclosed. The topsheet may be a laminate web having an upper layer of polymer film, directly bonded to a lower layer of nonwoven web. The film may include predominantly polyethylene (PE), have a basis weight of 8-20 gsm, and have formed thereon a pattern of cones and valleys, the cones projecting upwardly from adjacent valleys to rim edges proximate an upper side of the laminate web, the cones circumscribing and defining apertures through the film. The nonwoven web may have a basis weight of 12-24 gsm, and include staple fibers, with randomly-distributed fiber-to-fiber fusion bonds thereamong. The staple fibers may have an average denier of 3-12, and be spun of one or more polyolefins. Each of the film and the staple fibers may be modified with one or more hydrophilizing agents.

20 Claims, 10 Drawing Sheets

(51) Int. Cl.
    *A61F 13/511*     (2006.01)
    *A61L 15/24*     (2006.01)
    *A61L 15/48*     (2006.01)

(52) U.S. Cl.
    CPC ..... *A61L 15/48* (2013.01); *A61F 2013/15406* (2013.01); *A61F 2013/51147* (2013.01); *A61F 2013/51165* (2013.01)

(56) References Cited

U.S. PATENT DOCUMENTS

| | | | |
|---|---|---|---|
| 4,324,247 | A | 4/1982 | Aziz |
| 4,609,518 | A | 9/1986 | Curro et al. |
| 4,614,679 | A | 9/1986 | Farrington, Jr. |
| 4,626,254 | A | 12/1986 | Widlund |
| 4,629,457 | A | 12/1986 | Ness |
| 4,629,643 | A | 12/1986 | Curro |
| 4,798,604 | A | 1/1989 | Carter |
| 5,023,124 | A | 6/1991 | Kobayashi |
| 5,078,710 | A | 1/1992 | Suda |
| 5,368,909 | A | 11/1994 | Langdon |
| 5,368,910 | A | 11/1994 | Langdon |
| 5,567,376 | A | 10/1996 | Turi et al. |
| 5,674,211 | A | 10/1997 | Ekdahl |
| 5,919,177 | A | 7/1999 | Georger et al. |
| 5,935,682 | A | 8/1999 | Wallstroem |
| 6,096,016 | A | 8/2000 | Tsuji |
| 6,114,595 | A | 9/2000 | Moore et al. |
| 6,115,695 | A | 9/2000 | Kern |
| 6,168,849 | B1 | 1/2001 | Braverman et al. |
| 6,228,462 | B1 | 5/2001 | Lee |
| 6,417,426 | B1 | 7/2002 | Takai |
| 6,503,598 | B1 | 1/2003 | Goda |
| 6,608,236 | B1 * | 8/2003 | Burnes ................ A61F 13/5376 |
| | | | 604/385.01 |
| 7,102,054 | B1 | 9/2006 | Cree |
| 9,803,301 | B1 | 10/2017 | Maschino |
| 10,258,517 | B1 * | 4/2019 | Maschino ............... B32B 5/142 |
| 10,813,797 | B2 | 10/2020 | Cecchetto et al. |
| 2001/0014796 | A1 | 8/2001 | Mizutani |
| 2002/0026169 | A1 | 2/2002 | Takai |
| 2002/0052582 | A1 | 5/2002 | Takai et al. |
| 2002/0133132 | A1 | 9/2002 | Copat et al. |
| 2003/0003269 | A1 | 1/2003 | Lee et al. |
| 2004/0122396 | A1 | 6/2004 | Maldonado et al. |
| 2004/0161586 | A1 | 8/2004 | Cree |
| 2004/0176733 | A1 * | 9/2004 | Glaug ............... A61F 13/53713 |
| | | | 604/378 |
| 2004/0247833 | A1 | 12/2004 | Copat |
| 2005/0209575 | A1 | 9/2005 | Stone et al. |
| 2005/0234417 | A1 | 10/2005 | Yoshimasa |
| 2007/0196601 | A1 | 8/2007 | Ray |
| 2007/0212545 | A1 | 9/2007 | Cree |
| 2007/0255247 | A1 | 11/2007 | Moberg-alehammar |
| 2008/0132136 | A1 | 6/2008 | Uematsu et al. |
| 2008/0221538 | A1 | 9/2008 | Zhao |
| 2008/0221541 | A1 | 9/2008 | Lavash |
| 2008/0294135 | A1 | 11/2008 | Hara |
| 2009/0026651 | A1 | 1/2009 | Lee |
| 2009/0137976 | A1 | 5/2009 | Suzuki |
| 2009/0221979 | A1 | 9/2009 | Huang |
| 2009/0247977 | A1 | 10/2009 | Takeuchi |
| 2009/0302504 | A1 | 12/2009 | Di Berardino |
| 2010/0036339 | A1 | 2/2010 | Hammons |
| 2010/0036347 | A1 | 2/2010 | Hammons |
| 2010/0036349 | A1 | 2/2010 | Hammons |
| 2010/0069867 | A1 | 3/2010 | Noda |
| 2010/0247844 | A1 | 9/2010 | Curro |
| 2010/0255258 | A1 | 10/2010 | Curro et al. |
| 2011/0118691 | A1 | 5/2011 | Nishitani |
| 2011/0151185 | A1 | 6/2011 | Cree |
| 2011/0196330 | A1 | 8/2011 | Hammons |
| 2011/0221094 | A1 | 9/2011 | Gross |
| 2011/0223388 | A1 | 9/2011 | Stone et al. |
| 2011/0223399 | A1 | 9/2011 | Adachi |

| | | | |
|---|---|---|---|
| 2012/0003423 | A1 | 1/2012 | Cree |
| 2012/0064280 | A1 | 3/2012 | Hammons |
| 2012/0064298 | A1 | 3/2012 | Orr |
| 2012/0238984 | A1 | 9/2012 | Paldey |
| 2012/0273997 | A1 | 11/2012 | Stone |
| 2012/0277701 | A1 | 11/2012 | Stone |
| 2014/0120323 | A1 | 5/2014 | Lake et al. |
| 2014/0296815 | A1 | 10/2014 | Takken et al. |
| 2015/0038933 | A1 | 2/2015 | Day |
| 2015/0273793 | A1 | 10/2015 | Thomas |
| 2015/0297415 | A1 | 10/2015 | Huang |
| 2016/0038351 | A1 | 2/2016 | Cecchetto |
| 2016/0074259 | A1 | 3/2016 | Rosati et al. |
| 2016/0076181 | A1 | 3/2016 | Strube |
| 2016/0076184 | A1 | 3/2016 | Orr et al. |
| 2016/0158071 | A1 | 6/2016 | Barda |
| 2016/0158074 | A1 | 6/2016 | Norimoto |
| 2016/0257091 | A1 * | 9/2016 | Fornoni .................... B32B 3/30 |
| 2017/0258645 | A1 | 9/2017 | Orr |
| 2017/0297292 | A1 | 10/2017 | Maschino |
| 2018/0177643 | A1 | 6/2018 | Hao |
| 2019/0053960 | A1 * | 2/2019 | Saita ..................... A61F 13/534 |
| 2020/0060882 | A1 | 2/2020 | Cecchetto |
| 2020/0397628 | A1 | 12/2020 | Gwag et al. |
| 2021/0007907 | A1 | 1/2021 | Cecchetto et al. |

FOREIGN PATENT DOCUMENTS

| | | | |
|---|---|---|---|
| CN | 1943530 | A | 4/2007 |
| CN | 2905008 | Y | 5/2007 |
| CN | 2912578 | Y | 6/2007 |
| CN | 101438987 | A | 5/2009 |
| CN | 102140759 | A | 8/2011 |
| CN | 102555312 | A | 7/2012 |
| CN | 105411749 | A | 3/2016 |
| CN | 105496658 | A | 4/2016 |
| CN | 105581870 | A | 5/2016 |
| CN | 106064490 | A | 11/2016 |
| CN | 106313867 | A | 1/2017 |
| CN | 107718528 | B | 5/2023 |
| DE | 4437165 | A1 | 4/1996 |
| EP | 0403187 | A1 | 12/1990 |
| EP | 0489205 | A1 | 6/1992 |
| EP | 0738505 | A1 | 10/1996 |
| EP | 0749740 | A1 | 12/1996 |
| EP | 1022007 | A1 | 1/2000 |
| JP | S6472745 | A | 3/1989 |
| JP | H02102046 | A | 4/1990 |
| JP | H02193663 | A | 7/1990 |
| JP | H0452130 | A | 2/1992 |
| JP | H04187146 | A | 7/1992 |
| JP | H05125647 | A | 5/1993 |
| JP | H05228173 | A | 9/1993 |
| JP | H06330443 | A | 11/1994 |
| JP | 2002173863 | A | 6/2002 |
| JP | 2003000639 | A | 1/2003 |
| JP | 2003116909 | A | 4/2003 |
| JP | 2004275296 | A | 10/2004 |
| JP | 2006061174 | A | 3/2006 |
| JP | 2010063649 | A | 3/2010 |
| JP | 2010094320 | A | 4/2010 |
| JP | 2013078376 | A | 5/2013 |
| JP | 5829349 | B1 | 10/2015 |
| JP | 6206269 | B2 | 9/2017 |
| JP | 2647858 | B2 | 1/2021 |
| KR | 20110133188 | A | 12/2011 |
| KR | 20120018038 | A | 2/2012 |
| TW | 201225940 | A | 7/2012 |
| WO | 9311725 | A1 | 6/1993 |
| WO | 9700656 | A1 | 1/1997 |
| WO | 9702133 | A2 | 1/1997 |
| WO | 9711661 | A1 | 4/1997 |
| WO | 0025714 | A1 | 5/2000 |
| WO | 0059438 | A1 | 10/2000 |
| WO | 0117475 | A1 | 3/2001 |
| WO | 2005000177 | A1 | 1/2005 |
| WO | 2008058450 | A1 | 5/2008 |
| WO | 2010017353 | A1 | 2/2010 |
| WO | 2010110875 | A1 | 9/2010 |

(56)                References Cited

FOREIGN PATENT DOCUMENTS

| | | | |
|---|---|---|---|
| WO | 2011075669 | A2 | 6/2011 |
| WO | 2011080643 | A2 | 7/2011 |
| WO | 2012014957 | A1 | 2/2012 |
| WO | 2012024576 | A1 | 2/2012 |
| WO | 2013047868 | A1 | 4/2013 |
| WO | 2016019521 | A1 | 2/2016 |

OTHER PUBLICATIONS

Unpublished U.S. Appl. No. 18/811,116, filed Aug. 21, 2024, Pietro Cecchetto et al.
All Office Actions, U.S. Appl. No. 17/030,587, filed Sep. 24, 2020.
All Office Actions; U.S. Appl. No. 16/015,234, filed Jun. 22, 2018.
All Office Actions; U.S. Appl. No. 18/509,726, filed Nov. 15, 2023.
Unpublished U.S. Appl. No. 18/509,726, filed Nov. 15, 2023, to Pietro Cecchetto.

* cited by examiner z-upward x-y z-downward

22

16

21

20

17

| HV | HFW | W | mag ⊞ | 10/21/2020 | | | 1 mm |
| 5.00 kV | 5.18 mm | 14?? mm | 40 x | 8:56:05 AM | ⚠ ANALYTICAL | | ?per Analytical Micro NM |

20

25 y x

17

ABSORBENT ARTICLE WITH IMPROVED LAMINATE TOPSHEET

BACKGROUND

Absorbent articles such as feminine hygiene pads typically include a liquid permeable, wearer-facing topsheet, a liquid impermeable, outward-facing backsheet, and an absorbent structure disposed between the topsheet and the backsheet. The topsheet and backsheet are typically bonded together about and outside the perimeter of the absorbent structure, to envelope a space in which the absorbent structure is contained.

For feminine hygiene pads, it is generally desired that the liquid permeable topsheet readily accept and facilitate movement of discharged menstrual fluid quickly therethrough down to the underlying absorbent components of the absorbent structure, to minimize spreading flow of discharged fluid across the topsheet surface, and thereby reduce a risk that fluid may escape the pad and soil the user's underwear, outer clothing, bedding, etc. It is also generally desired that the topsheet not absorb or retain fluid itself, but rather, readily pass it to underlying absorbent components, so that it will feel dry to the user after a discharge of fluid to the pad. Generally, it is desired that the topsheet have a soft, compliant, cool, cloth-like feel against the wearer's skin, and that it not generate noise when manipulated during application or moved about against the user's body during use/wear. It is also generally desired by users that the topsheet have a level of opacity that enables it to conceal, to a feasible extent, fluid that has passed therethrough and been retained in the underlying absorbent structure.

The topsheet material also should be sufficiently mechanically robust to pass without unworkable degrees of stretchability or tearing failure, through pad manufacturing process equipment. Conservation of material usage, manufacturing efficiency and cost control are ever-present objectives.

From the perspective of engineering material(s) to be used to form a topsheet, these objectives are in conflict to varying degrees, and it is difficult to serve all of them simultaneously.

Toward attempting to serve these objectives, laminate webs including an apertured polymeric film layer and a fibrous nonwoven web layer have been developed, with varying degrees of success. There are myriad varying possible permutations of combinations of materials compositions, quantities, physical structures and dimensions, and orientations of features, of the film layer and of the nonwoven web layer, and in the manner in which they are joined to form a laminate. Selecting from among these permutations can result in a topsheet material that is, unpredictably, relatively successful at serving the objectives identified above, or not. Opportunities remain for exploration, discovery and improvement in selections of combinations of these variables and permutations, to form an improved consumer/user-pleasing, functionally successful and cost-effective topsheet material.

DETAILED DESCRIPTION OF EXAMPLES

Figure 1:
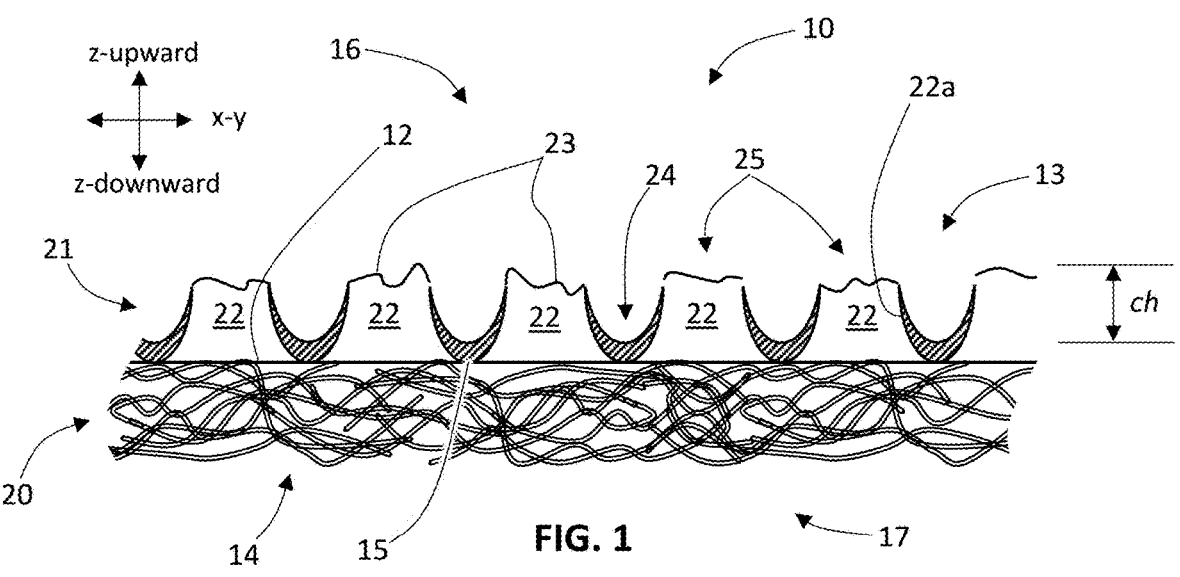
FIG. 1 is a schematic, expanded vertical cross section view of a portion of an example of a laminate web as contemplated herein.
Figure 2A:
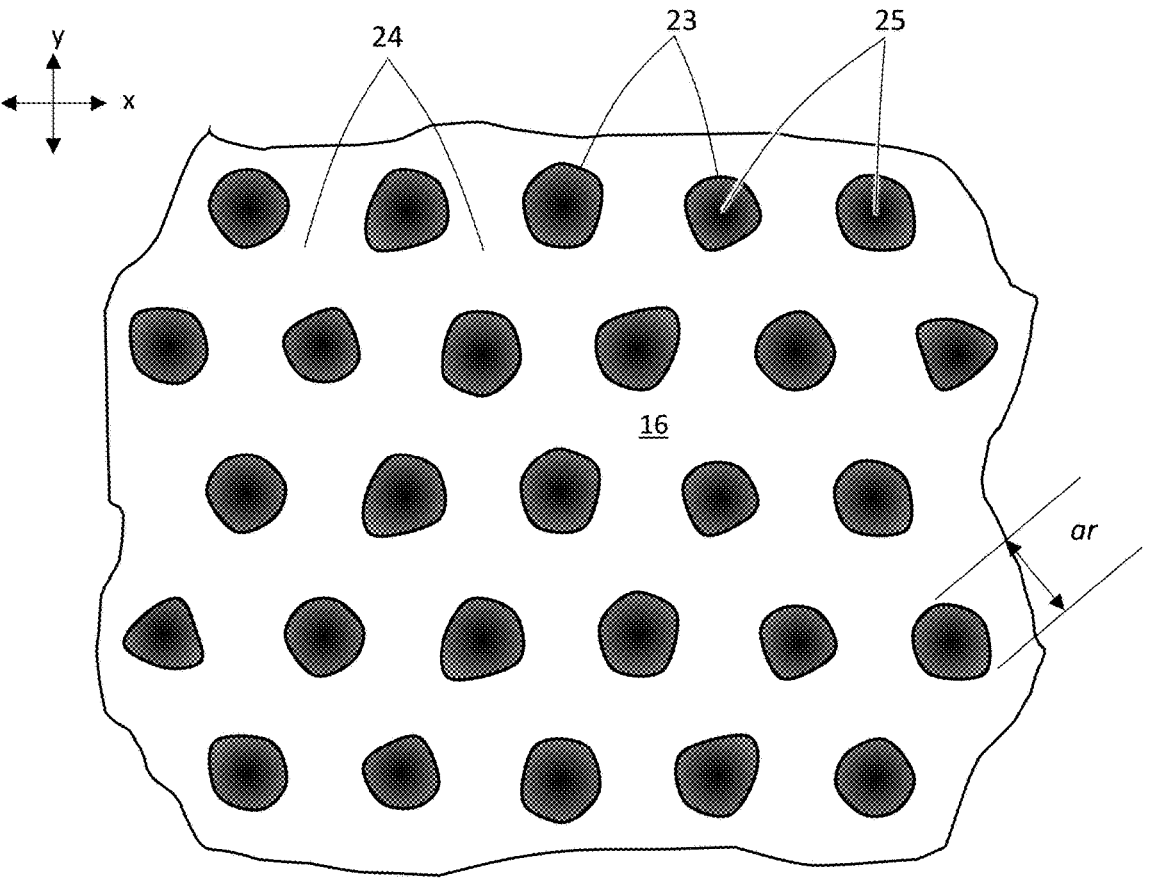
FIG. 2A is a schematic, expanded x-y plan view of the upper side of a portion of an example of a laminate web as contemplated herein.
Figure 2B:
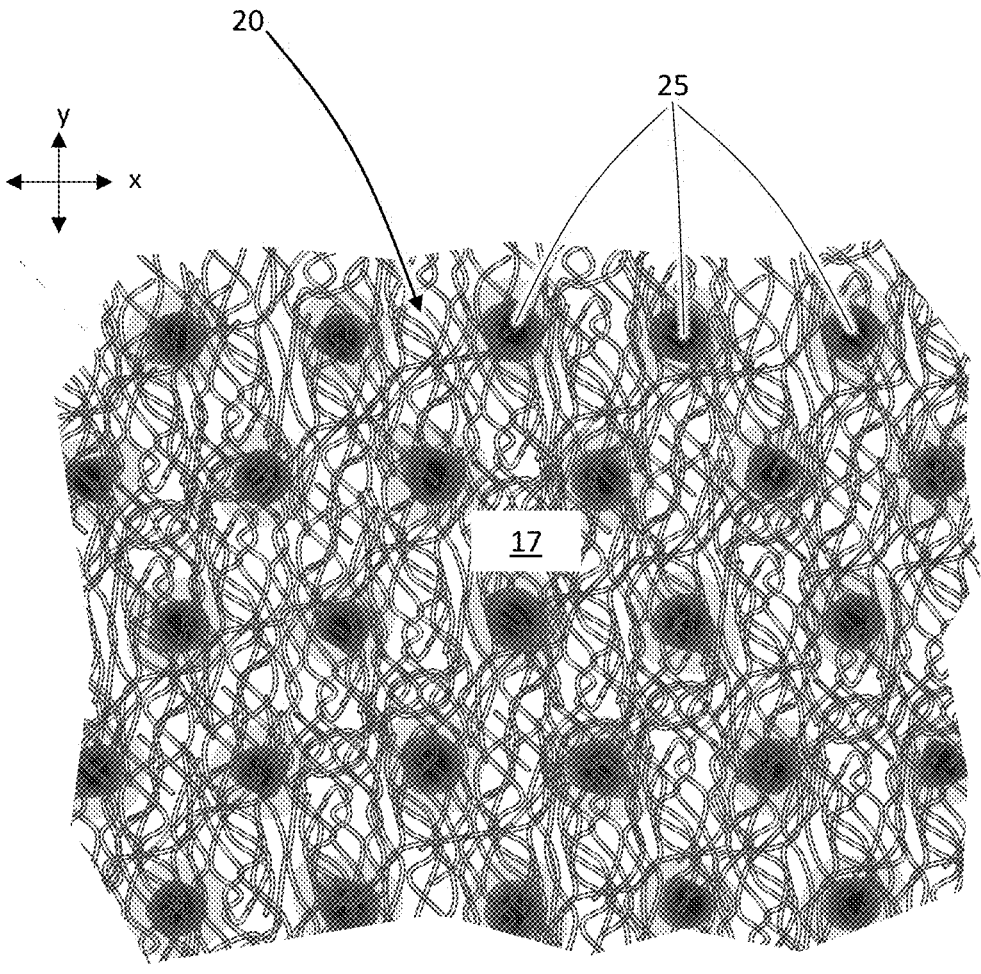
FIG. 2B is a schematic, expanded x-y plan view of the lower side of a portion of an example of a laminate web as contemplated herein.

The term "absorbent article" includes disposable articles such as feminine hygiene pads (sometimes called "sanitary napkins"), panty liners, diapers and training pants, menstrual underwear, adult incontinence pads and absorbent underwear. Such absorbent articles are designed for the absorption of body exudates, such as menstrual fluid, urine, and liquidous feces. Absorbent articles contemplated herein will typically include a liquid permeable topsheet, a liquid impermeable backsheet joined to the topsheet, and an absorbent structure disposed between the topsheet and backsheet.

The term "absorbent structure", as used herein, refers to the component or combination of components of the absorbent article that is adapted for absorbing and retaining absorbed liquids until such time the wearer/user removes the article from wear/use.

The term "aperture", as used herein, refers to a hole through a film and/or other web material. Apertures may be punched through the web material so that material of the web circumscribing the aperture is disposed approximately in the same plane occupied the web prior to the formation of the aperture; or apertures through a web may created in a manner in which at least some of the web material circumscribing the aperture is deformed and displaced in a z-direction out of an original plane occupied by the web. In the latter case, the apertures may be circumscribed by a deformation of the web material.

Herein, use of the term "cone" is not intended to mean or imply compliance of the shape of the feature referred to with the definitions of "cone" or "conical" in mathematics or geometry. Rather, it is intended as a shorthand expression to describe formations in a film that result from a deformation-based aperturing process as described herein. The formations referred to as "cones" herein may be varying and irregular in shape, as reflected in the figures.

The term "cross direction" or "CD", as used herein with respect to a web, refers to the path that is perpendicular to the machine direction and along the plane occupied by the web.

The term "machine direction" or "MD", as used herein with respect to a web, refers to the path that the web follows through a manufacturing process.

For an absorbent article or component thereof laid out flat along a horizontal plane, the term "z-direction" refers to a direction orthogonal to the horizontal plane. For an absorbent article or component thereof that is applied to and/or being worn by a wearer, the "z-direction" at any particular location on the article is a direction generally normal to the curvature of the article or component at that location, as it follows or wraps about the wearer's body contours.

For a component or feature of an absorbent article, the vertical references "upper", "lower", "uppermost", "lowermost", "height," and similar terms characterizing vertical positioning or vertical dimensions, refer to positioning or dimension of the component or feature relative other components or features and relative a wearer's body when the article is used/worn. An "upper" component or feature is disposed relatively nearer the wearer's body than a "lower" component. When the article is laid out flat on a horizontal surface with wearer-facing surface facing up, the "upper" surfaces of layer components face upwardly and the "lower" surfaces of layer components face downwardly.

The term "predominantly", when used with respect to a quantity of numerical count, weight, volume or linear dimension of a component present in a structure, means that a majority of the numerical count, weight, volume structure is constituted by the component.

With respect to apertures or cones present in a film, "numerical density" refers to the number of apertures present per unit x-y plane surface area of the film on one side.

Laminate Web

Referring to FIGS. 1 through 4D, a laminate web 10 contemplated herein includes a nonwoven layer 20 of nonwoven web, and a polymer film layer 21 of polymer film. The nonwoven layer 20 has an upper surface 12 and a lower surface 14, and film layer 21 has an upper surface 13 and a lower surface 15. Web 10 has a machine direction (MD) and a cross machine direction (CD) as are commonly understood in the art of web manufacturing. The layers are described herein as generally planar, having major sides lying along x-y planes and having a caliper measured along the z-direction. The nonwoven layers 20 and the film layer 21 (and any additional layer(s)) can be joined by adhesive, thermal bonding, ultrasonic bonding or by other mechanisms. In some examples, the fibrous nonwoven web and film may be joined by applying the nonwoven web to an extruded film after the film has emerged from the extruding die but is still partially molten, whereupon some fibers of the nonwoven web will adhere to or bond with the molten film, provided other features and processes facilitating such adhesion or bonding are included. For example, where the polymer constituent(s) of the film and of the fibers have compatible chemistries (i.e., they are miscible with each other in the melted phase), some fibers contacting the partially molten film may fuse with the molten film, provided that suitable processing steps and conditions are appropriately provided and adjusted.

Web 10 has an upper side 16 and a lower side 17. The term "sides" is used in the common usage of generally planar webs, such as paper and films that have two major sides when in a generally macroscopically flat condition.

The nonwoven layer 20 and film layer 21 in the laminate contemplated herein can have an opacity. To enhance opacity to a desired level, the manufacturer may blend into one or more fiber component resin(s) a pigmenting, whitening, or opacifying agent (for example, TiO$_2$ powder), in a quantity of at least 1% to 5%, more preferably 1% to 3%, by weight of the nonwoven layer. In addition, or alternatively, the manufacturer may blend a pigmenting, whitening, or opacifying agent (for example, TiO$_2$ powder) into the component resin(s) of the film layer, such as TiO$_2$ in a quantity of at least 1% to 10%, more preferably 5% to 9%, and even more preferably 6% to 8%, by weight of the film layer. In some examples, the film layer may have a higher weight percent quantity of whitener than the nonwoven layer. The selected pigmenting, whitening, or opacifying agent is preferably an inorganic pigmenting agent that will not degrade or change chemically at temperatures at which the polymers are spun or extruded, and not chemically react with the polymer resin(s) into which it is blended. It is generally desired to achieve as much opacity as possible, while not substantially weakening the structures of the fibers or film by overloading, and not causing excessive die wear that may be caused by abrasive inorganic pigment particles in a resin blend, rubbing again fiber spinning and film extruding dies. In some examples, a whitening agent such as TiO$_2$ powder may be preferred because consumers/users of absorbent articles may tend to associate white coloration with cleanliness, purity and or sanitariness.

Nonwoven Layer

A laminate web contemplated herein includes a nonwoven layer of nonwoven web material.

As used herein, the term "nonwoven web" refers to a web having a structure formed of individual fibers which are accumulated, consolidated and held together in a cohesive web in somewhat random orientations, but are not knitted or woven together. Nonwoven webs may be manufactured via a variety of processes, such as, for example, meltblowing processes, spunbonding processes, airlaying and hydroentangling, and bonded carded web processes, including carding followed by thermal bonding (e.g., air-through bonding). The fibers may be staple fibers, or may be continuous fibers. The fibers may be accumulated in a continuous process on a moving forming belt, to form a batt having a desired basis weight level, and then consolidated and further processed (e.g., bonded) to impart cohesion and create a fabric-like web. The basis weight of nonwoven fabrics is usually expressed in grams per square meter (gsm). The basis weight of the laminate web is the combined basis weight of the constituent layers and any other added components. Fiber diameters are usually expressed in microns (μm); fiber size can also be expressed indirectly via denier value. The basis weight of laminate webs contemplated herein can range from 10 gsm to 500 gsm, depending on the ultimate use of the laminate web.

The constituent fibers of the nonwoven web may be formed of polymers such as polyethylene, polypropylene, polyester, and blends thereof. The fibers may also include cellulose, rayon (or other fibers spun from regenerated cellulose), cotton, or other natural plant fibers, or blends of spun polymer fibers and semisynthetic and/or natural plant fibers. The fibers may be spun as monocomponent, bicomponent, and/or biconstituent, non-round (e.g., protrusionillary channel fibers), and can have major cross-sectional dimensions (e.g., diameter for round fibers) ranging from 0.1-500 μm. The constituent fibers of the nonwoven precursor web may be a blend of different fiber types, differing in such features as component chemistry (e.g. polyethylene and polypropylene), component configuration (e.g. monocomponent, bicomponent, etc.), cross-section shape (e.g., protrusionillary or round), etc. The constituent fibers can range from about 0.1 denier to about 400 denier.

For purposes contemplated herein, it may be preferred that the nonwoven web not include any substantial quantities of natural plant fibers or fibers spun from regenerated cellulose. This is because such fibers and nonwoven web materials including them as constituents tend to absorb and retain aqueous liquids. For a topsheet as contemplated herein, it is not desirable that the nonwoven layer 20 absorb or retain aqueous liquid, but rather that it readily pass fluid to an underlying absorbent structure. Accordingly, it may be desired that the nonwoven layer 20 include no more than 10%, more preferably no more than 5%, and even more preferably no more than 2%, by weight, natural plant fibers or fibers spun from regenerated cellulose.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer or only one homogeneous blend of compatible polymers. (Herein, "compatible polymers" are two or more polymers that are miscible and will, with mechanical agitation, form a stable homogeneous mixture/blend, at the melting temperature of the polymer with the higher melting temperature). This is not meant to exclude fibers formed from one polymer or homogeneous blend to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers and/or homogeneous polymer blends, spun together through appropriately designed spinnerets to form a single fiber having a cross section with identifiable regions each formed of one or the other polymer or blend. Bicomponent fibers are also sometimes referred to as conjugate fibers or multicomponent fibers. The polymers are arranged in distinct zones across the cross-section of the bicomponent fibers, and the zones extending continuously along the lengths of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Sheath/core arrangements may be concentric/coaxial, or eccentric. In the latter, the core component is arranged to be off-center with respect to the sheath component. If the selected polymers constituting the individual fiber components have differing contraction rates upon cooling, a side-by-side, eccentric sheath/core, or other eccentric component configuration may cause the fibers to curl or crimp following spinning and upon cooling, which may be desired in some applications, for example, to add loft to the nonwoven web in which the fibers are to be constituents.

As used herein, the term "biconstituent fibers" refers to fibers which have been formed from at least two polymers and/or homogeneous blends, extruded from the same extruder as a non-homogeneous formation having discrete but randomly-formed zones of one polymer and/or homogeneous blend, or the other. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" describes fibers having a non-round cross-section, and includes "shaped fibers" and "protrusionillary channel fibers." Such fibers can be solid or hollow, and they can be tri-lobal, delta-shaped, and are preferably fibers having protrusionillary channels on their outer surfaces. Protrusionillary channels can be of various cross-sectional shapes such as "U-shaped", "H-shaped", "C-shaped" and "V-shaped", star-shaped, etc.

A nonwoven layer may include fibers having sufficient elongation properties to have portions elongated. The portion elongated are formed by urging fibers out-of-plane in the Z-direction at discrete, localized, portions of the nonwoven layer. The urging out-of-plane can be due to fiber displacement, i.e., the fibers are able to move relative to other fibers and be "pulled," so to speak, out-of-plane. More often, however, for most nonwoven layers suitable for the laminate web contemplated herein, the urging out-of-plane is due to the fibers having been at least partially plastically stretched and permanently deformed.

The nonwoven layer useful for the laminate web contemplated herein may include a nonwoven web constituted of substantially randomly oriented fibers. By "substantially randomly oriented" is meant that, due to processing conditions for producing the precursor nonwoven web, there may be a higher number of fibers generally oriented in the machine direction than the cross direction, or vice-versa, but beyond such general orientation the fibers are randomly laid.

The nonwoven layer may have a basis weight of 10 gsm to 60 gsm, 12 gsm to 25 gsm, or 12 gsm to 18 gsm, or most preferably 14 gsm to 16 gsm. In general, when used to form the nonwoven layer 20 of the laminate 10 contemplated herein, in turn used to form a topsheet, nonwovens of higher basis weights result in relatively lower/slower fluid acquisition speeds, although laminate 10 opacity (and thus capability for concealing staining in the absorbent structure) may be increased. The nonwoven web layer 20 is included to impart structural integrity to the laminate web 10, to provide absorbent structure stain concealment, and to provide some space between the uppermost film layer and the underlying absorbent structure components to enhance fluid acquisition help prevent rewetting of the wearer-facing upper surface 16 of the laminate 10.

In some examples contemplated herein, the nonwoven layer 20 may exhibit a median distance between two adjacent fibers in a z-direction of above about 55 μm, or from 60 to 200 μm, when measured according to the Fiber-Fiber Distance Measurement method described herein. When the nonwoven layer 20 is formed of carded fibers, the nonwoven can be manufactured to have a median distance between two adjacent fibers in a z-direction of 55 μm or greater, up to about 200 μm, by adjusting production conditions such as oven air temperature (in a through-air bonding process), hot air velocity, and nonwoven web tension, when the web goes through the oven and/or calendar rolls, in order to retain or enhance caliper of the resulting nonwoven web. For example, increasing oven air temperature reduces caliper of the resulting nonwoven web, and increasing hot air velocity reduces caliper of the resulting nonwoven web. In addition, increasing web tension in the through-air bonding process may reduce caliper of the resulting nonwoven web. Accordingly, controlling/limiting these process variables can help preserve caliper of the resulting nonwoven web. In addition, or alternatively, fiber denier may be selected and controlled. Additionally, generally, selection of higher denier fibers as constituents of the nonwoven layer 20 will cause the nonwoven layer to have greater median fiber-fiber distance, and vice versa. Selection of denier, however, is also influenced downwardly by the need for pliability and softness of the laminate web 10.

In some examples, the nonwoven web used to form nonwoven layer 20 is formed of carded polymer staple fibers of have an average denier of 3-12, more preferably 5-9, and even more preferably 5-7. In combination with fiber composition more specifically described below, manufacturing fibers to a denier within one or more of these ranges strikes a suitable balance between fiber pliability and, as result, overall web pliability and perceivable softness, and fiber stiffness, and, as a result, maintenance of caliper of the nonwoven layer 20 for suitable fluid handling performance. Generally, when the laminate 10 contemplated herein is used to form a topsheet for an absorbent article, it is desired that the nonwoven layer be capable of retaining its uncompressed z-direction caliper as much as possible and feasible, for purposes of maintaining void space between topsheet material and underlying components of an absorbent structure.

Figure 3A:
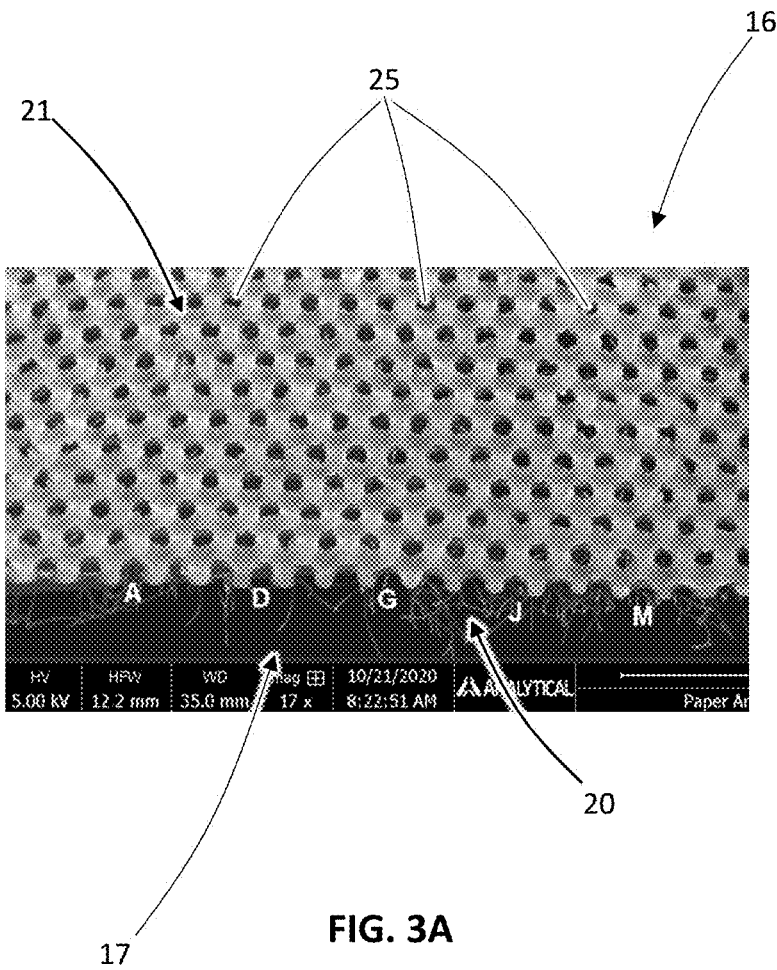
FIG. 3A is a photograph of a magnified perspective view of a portion of an example of a laminate web as contemplated herein.
Figure 3B:
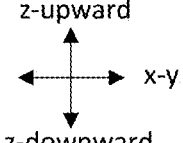
FIG. 3B is a photograph of a magnified vertical section of a portion of an example of a laminate web as contemplated herein.
Figure 3C:
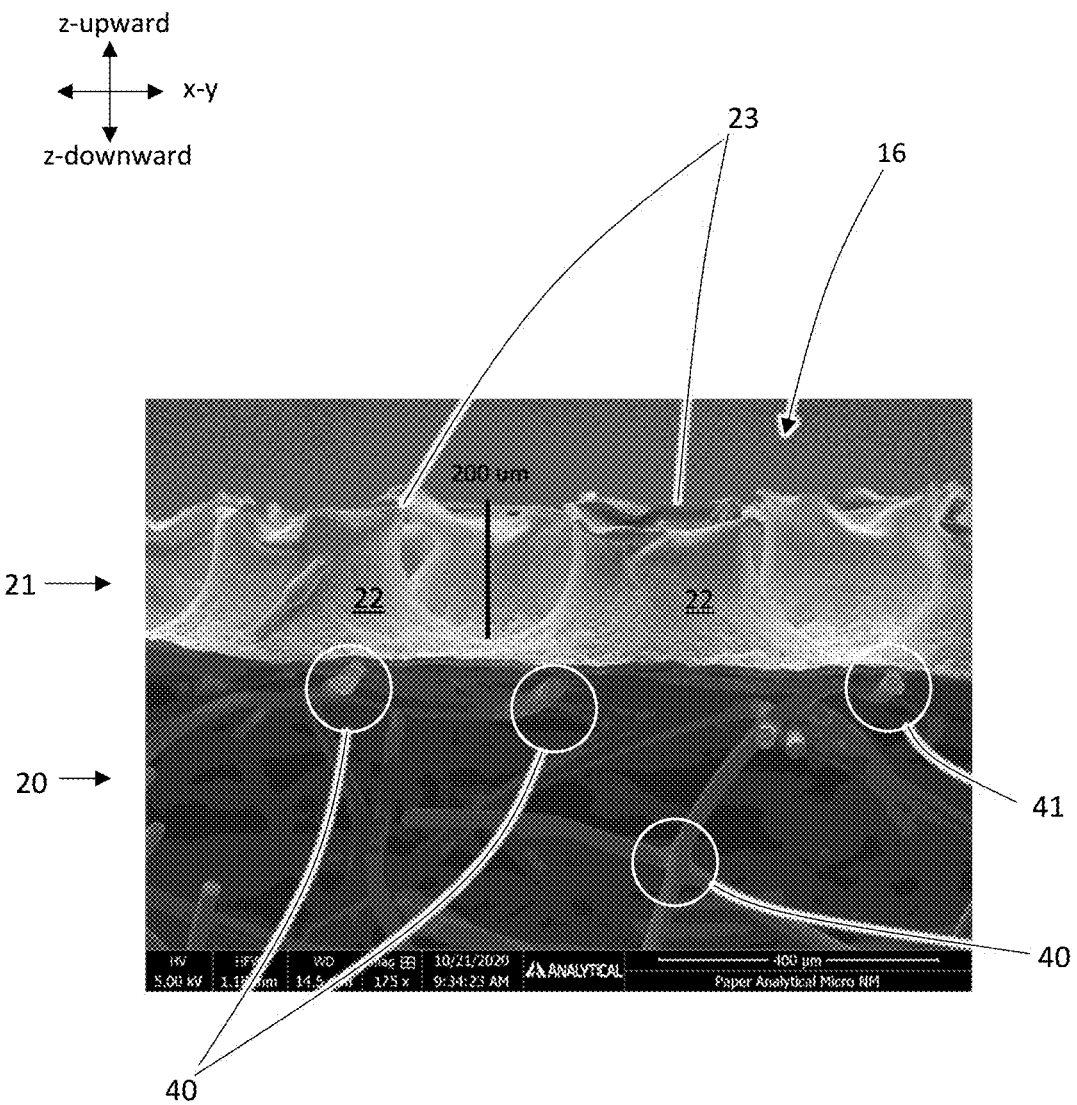
FIG. 3C is a photograph of a further-magnified vertical section of a portion of an example of a laminate web as contemplated herein.
Figure 4A:
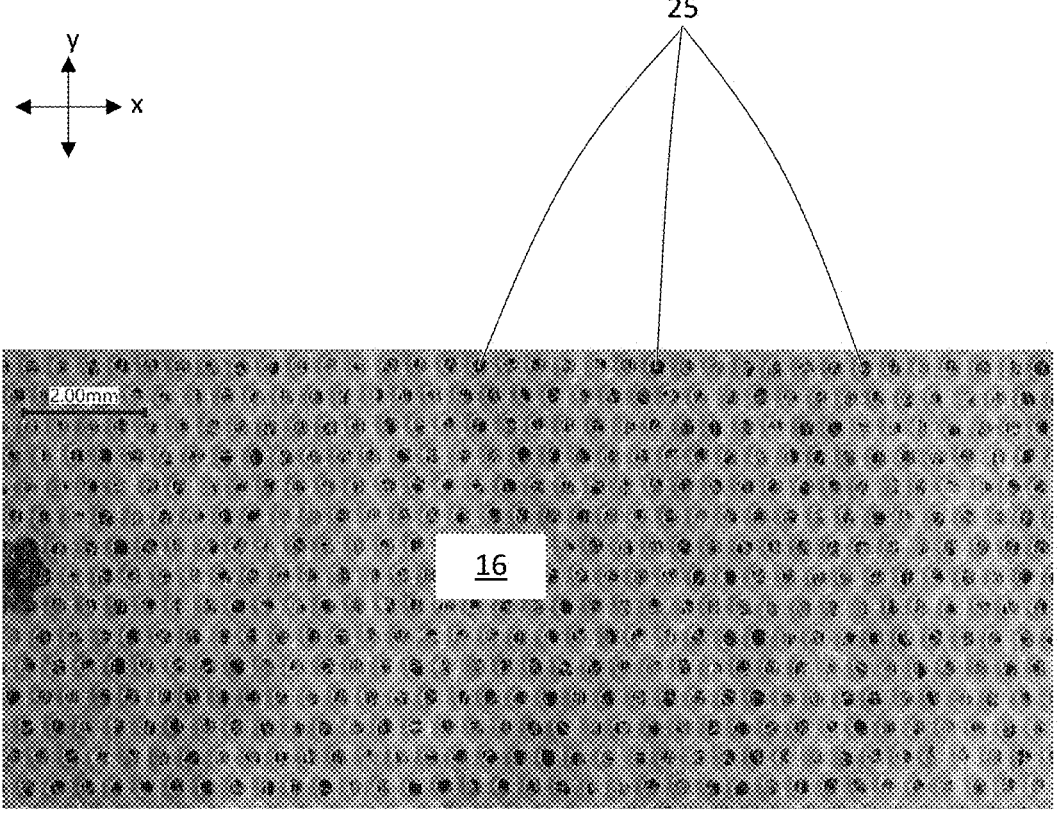
FIG. 4A is a photograph of a magnified plan view of the upper side of a portion of an example of a laminate web as contemplated herein.
Figure 4B:
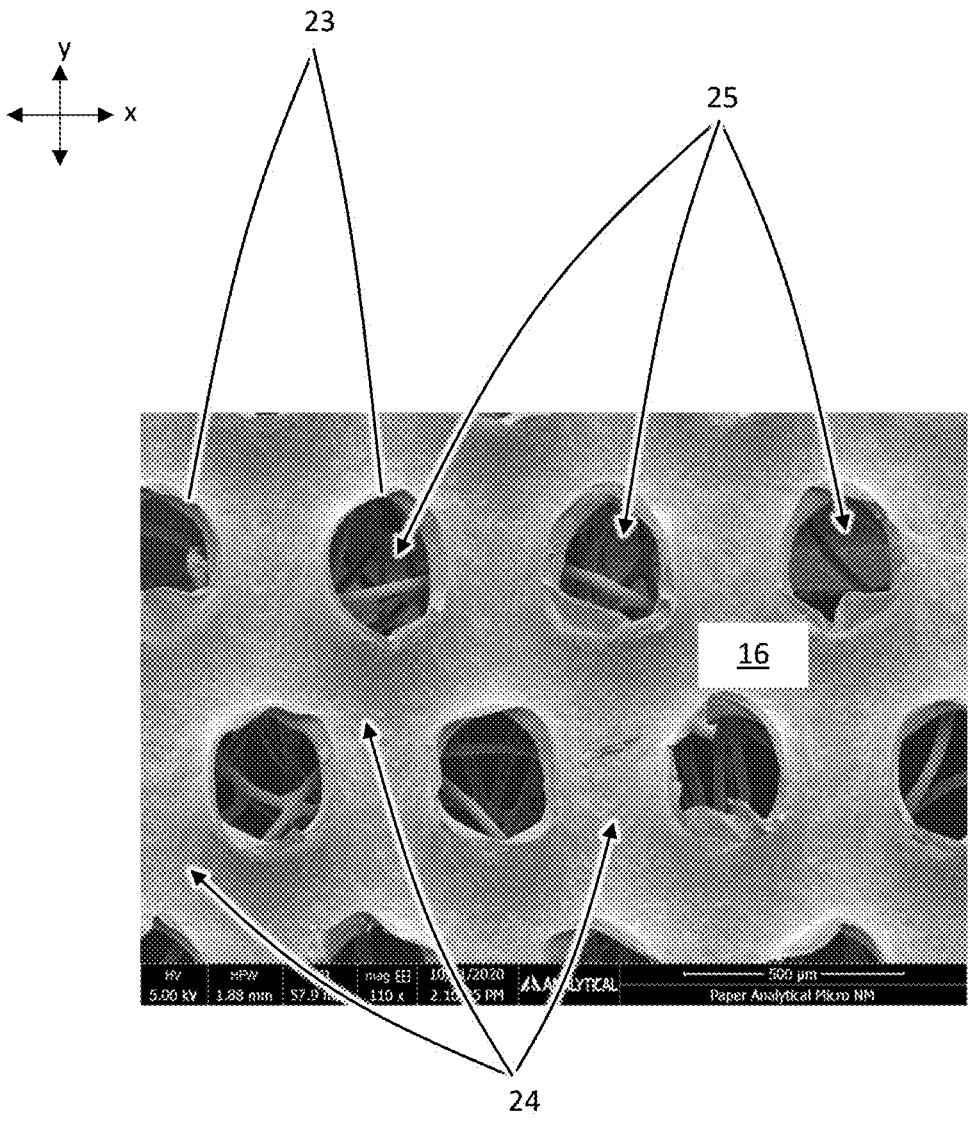
FIG. 4B is a photograph of a further-magnified plan view of the upper side of a portion of an example of a laminate web as contemplated herein.
Figure 4C:
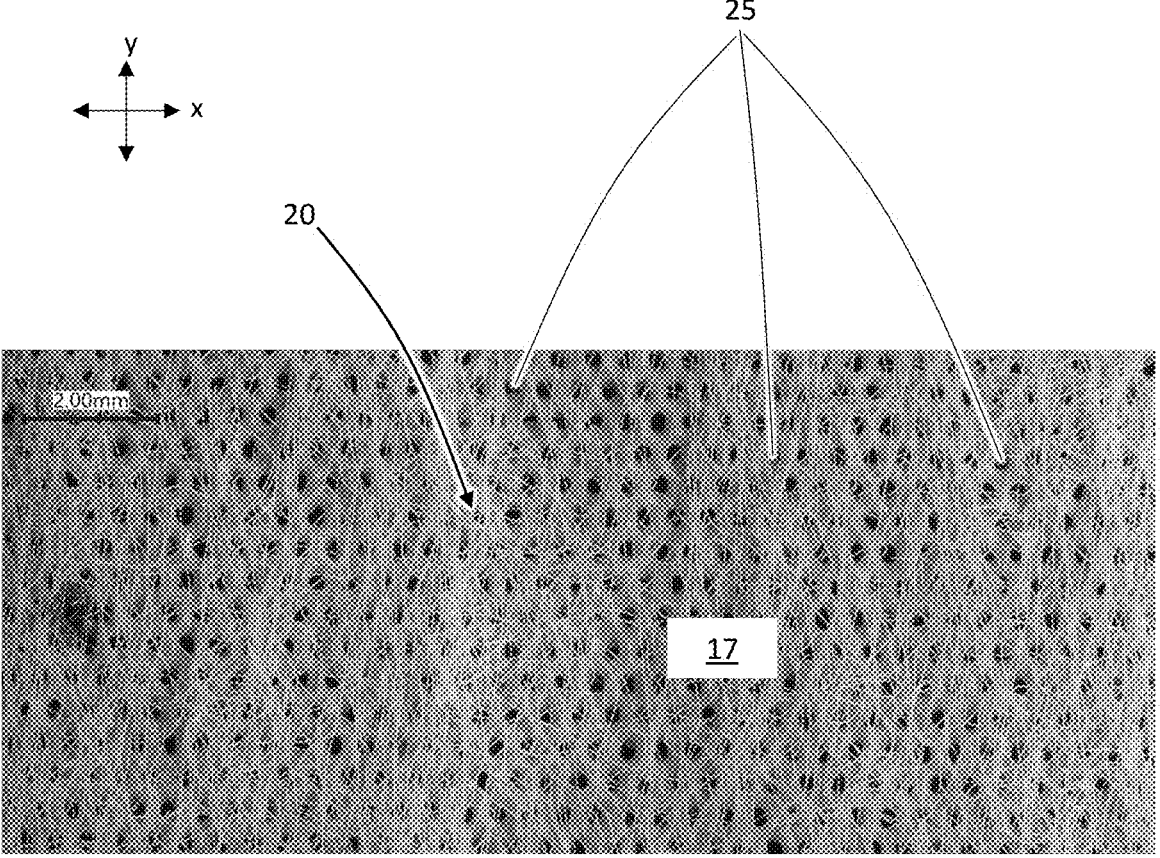
FIG. 4C is a photograph of a magnified plan view of the lower side of a portion of an example of a laminate web as contemplated herein.
Figure 4D:
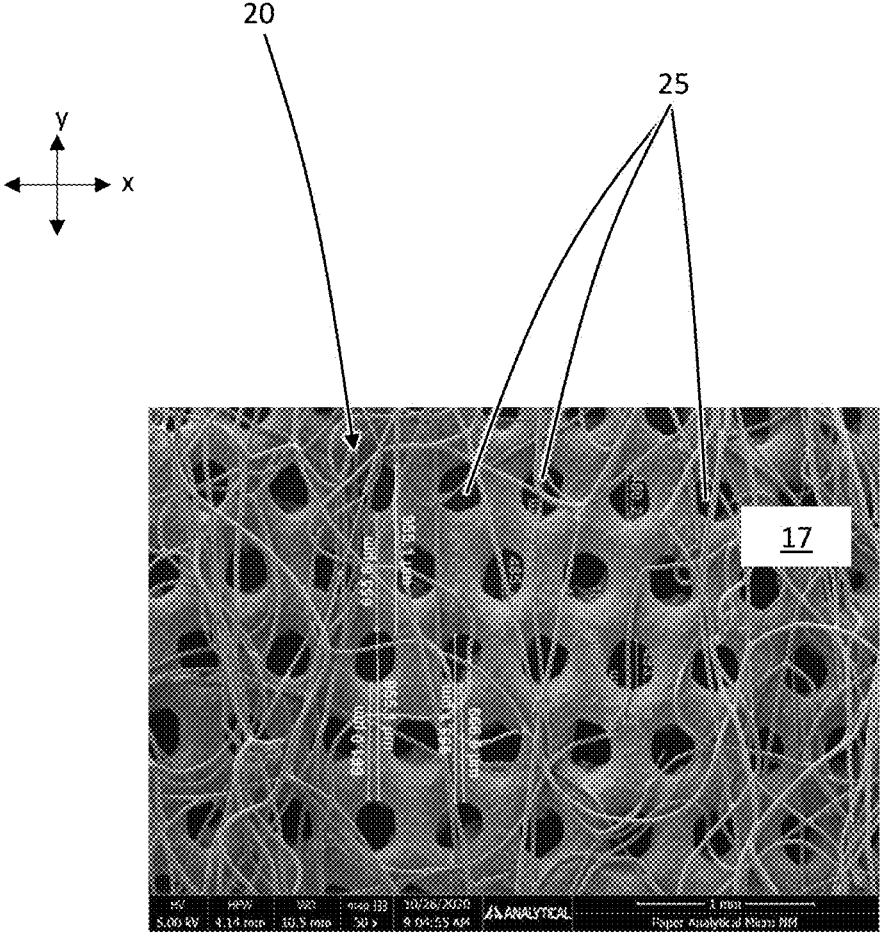
FIG. 4D is a photograph of a further-magnified plan view of the lower side of a portion of an example of a laminate web as contemplated herein.

In combination with features described above, in some examples, the constituent fibers of the nonwoven layer 20 include, predominantly or substantially entirely, bicomponent fibers, and preferably bicomponent fibers of a sheath-core arrangement. The polymer for the core component may be selected to be predominately or substantially entirely polyethylene terephthalate (PET), while the polymer for the sheath component may be selected to be predominately or substantially entirely a polyolefin such as polyethene. This choice of fiber components and configuration provides several advantages. When spun into a fiber, PET is relatively stiff, and imparts resilience to the fiber, which is particularly advantageous when fibers of relatively low denier are desired. On the other hand, a polyolefin such as polyethylene will have a relatively lower melting temperature than the PET, such that the fibers are particularly well-suited for controlled through-air bonding of the web, such that the polyolefin (e.g. polyethylene) sheath components of adjacent fibers can partially melt and fuse together at random locations so as to result in a cohesive web, while the PET core components do not melt and do not substantially deform in the bonding process, such that caliper of the resulting nonwoven web can be maximized. In FIG. 3C, several of these randomly-disposed fiber-to-fiber bonds 40, resulting from a through-air bonding process for such fiber constituents, may be seen. The fiber spinning process may be configured such that sheath and core components of the spun fibers are present in a weight ratio of 65:35 to 35:65, 60:40 to 60:60, 55:45 to 45:55, or even approximately 50:50. Generally, increasing the proportion of PET will result in stiffer fibers but reduced bond formation or less robust bonds, and vice versa. Through-air bonding, in which heated air is driven through the batt of constituent fibers to form fiber-to-fiber bonds and a resulting cohesive web, may be preferred over other methods of bonding that require z-direction compression of the web, which reduces caliper and intra-fiber space volume. Through-air bonding results in randomly-distributed fiber-to-fiber bonds that do not exhibit evidence of z-direction compression of the batt or web, through mechanically-applied compressing force (e.g., as is typified by thermal/compression calender bonds in a spunbond nonwoven web material).

Generally the fiber polymer components contemplated herein will be naturally hydrophobic, and upon spinning will form fibers with hydrophobic surfaces. Thus, without added processing or materials, the fibers may be somewhat resistive to movement of aqueous fluid along their surfaces, and thus, through intra-fiber spaces through the nonwoven layer 20. However, it is desired that the nonwoven layer 21 readily accept and facilitate passage of aqueous fluid (such as menstrual fluid) therethrough. Accordingly, the constituent fibers of the nonwoven layer 20 may be surface-treated with a suitable hydrophilizing agent such as a surfactant, either before or after formation of the nonwoven layer component, or before or after formation of laminate web 10. Alternatively, or in addition, the polymer components of the fibers may have blended thereinto, prior to fiber spinning, a hydrophilizing agent, suitably selected to be blended with the polymer component(s) in melt and then migrate through the individual fiber structures, and "bloom" out to the surfaces of the fibers. Where the fibers are bicomponent fibers of a sheath/core arrangement as described above, it is preferred that such a blooming hydrophilizing agent be blended into the polymer constituent of the sheath component.

Film Layer

Referring to FIGS. 1 through 4D, film layer 21 of laminate web 10 may be cast, extruded or formed by other film formation processes, of one or more polymer components. In its finally formed state the film layer 21 may include a pattern of cone formations ("cones") 22 formed therein. A corresponding pattern or arrangement of valleys 24 is present between the cones 22. The cones 22 extend in an upward direction from the valleys and terminate in cone rim edges 23. The rim edges 23 and/or inner wall surfaces 22a of the cones 22 circumscribe apertures 25 through the film layer, which may be viewed along the z-direction and seen to define areas along an x-y plane.

The z-direction orientation, shapes, dimensions, geometric features and numerical density of the cones 22 and apertures 25, as well as the composition and basis weight of film layer 21, will impact the relative degree of success or failure of the laminate 10 at meeting the objectives for an absorbent article topsheet, as identified herein.

It has been learned to be preferable that the cones 22 project upwardly from the valleys 24 (for a topsheet, toward the wearer/user), rather than downwardly toward the nonwoven layer 20 and underlying absorbent components. This feature, combined with a suitable level of numerical density of the cones/apertures, provides for a film that largely contacts the wearer/user's skin primarily at the cone rims 23, providing for intermittent/discontinuous areas of contact between the wearer's skin and the film layer 21. For a topsheet of an absorbent article, the result is that the upper film layer 21 component, desirably, feels less like plastic film, and more like fibrous fabric, against the user/wearer's skin.

It has been learned that one or a homogeneous blend of polyethylene (PE) variants including low-density PE (LDPE) and linear low-density PE (LLDPE) are preferable as polymer components of film layer 21. These are preferred because they have relatively low melting temperatures, and when the film layer precursor component is joined with a nonwoven web precursor component including fiber constituents having relatively higher melting temperatures, the film layer precursor component may be deformed to form cones 22 with minimized risk of melting the higher-melttemperature fiber constituents, which may cause loss of caliper of the nonwoven layer. Additionally, it has been learned that cones formed in a film constituted of one or a combination of LDPE and LLDPE contribute substantially to a soft skin feel for the upper side 16 of the laminate web. Generally, LDPE tends to be softer and more pliable, contributing to soft feel, while LLDPE tends to provide more stiffness/rigidity, contributing to maintaining structural integrity of the cones. When the cones 22 are formed in the film via a process described below, the film is stretched to rupture to form apertures through the cones/film, and the rim edges 23 are relatively thin from stretching prior to rupture. These rim edges contact the user's skin during use, and when the film is constituted of LDPE (supplemented by LLDPE), are quite pliable and feel soft, particularly when the cones are arranged with a size and numerical density as described herein. For this reason such constitution of film layer 21 has been discovered to be preferable to other combinations of potential film components such as high-density PE (HDPE), polypropylene, PET, etc. These other polymers when included may impart a relatively undesirable level of stiffness to the film layer and the cones, which contributes to maintaining structural integrity of the cones—but this comes at the cost of soft skin feel for the user. A film layer having cones that are too stiff may actually feel scratchy to the user. It has been learned, however, that constituting the film layer 21 only of one or a blend of LDPE and LLDPE provides for cones that sufficiently maintain structure integrity while still being pliable and impart a soft skin feel to the upper side 16 of the laminate 10. Accordingly, the film layer 21 contemplated herein preferably is constituted of no more than 10%, more preferably no more than 5%, and even more preferably no more than 1%, HDPE, polyethylene or PET.

Like polymer constituent fibers of the nonwoven layer 20, the polymer component(s) of the film layer 21 may be naturally hydrophobic, and result in formation of a film that does not facilitate movement of aqueous fluid (such as menstrual fluid) along its surfaces and thus down through cones 22 and apertures 25, to underlying layers. However, it is desired that film layer readily accept and facilitate passage of aqueous fluid through the apertures 25. Accordingly, film layer 21 may be surface-treated with a suitable hydrophilizing agent such as a surfactant, either before or after formation of the laminate web 10. Alternatively, or in addition, the polymer component(s) of the film layer 21 may have blended thereinto, prior to formation of the film, a hydrophilizing agent, suitably selected to be blended with the polymer component(s) in melt and then migrate through the film structure, and "bloom" out to the surfaces of the film.

The precursor film may be formed by any suitable process, for example, via extrusion of molten polymer constituents through a film extrusion die.

Polymeric film having cones 22 can be provided using any process generally known in the art; however, it will be understood that selections of materials, quantities and process variables, including but not limited to film composition, film basis weight, forming apparatus geometry, formation temperatures, throughput speed, and composition of nonwoven layer 20, will impact the relative success or failure of the resulting laminate web 10 contemplated herein.

As noted, a film layer 21 with cones 22 will provide the exterior surfaces of the web with a softer, more cloth-like texture, provide the web with a more cloth-like appearance, and increase the overall caliper of the web. Examples of processes to cones 22 in a film include but are not limited to vacuum formation and mechanical deformation, and any combination thereof.

The film layer may be extruded to have a basis weight of between about 8 gsm to about 35 gsm, between about 10 gsm to about 20 gsm, or between about 10 gsm to about 14 gsm. If the film is manufactured to a basis weight less than 8 gsm, it may be unacceptably vulnerable to tearing in downstream manufacturing processes, or in use of an absorbent article in which the laminate 10 is a topsheet component as contemplated herein. If the film layer is manufactured to a basis weight greater than 35 gsm, it may be unacceptably stiff and impart unacceptable stiffness to the laminate 10, and reliable formation of cones with apertures and features described herein may be adversely impacted.

Cones

The film layer 21 of laminate web 10 contemplated herein includes a pattern of cones 22 formed in the film. The cones 22 may be imparted with open upper ends, terminating in rim edges 23 and having side walls 22a. The laminate 10 may be configured such that the cones 22 extend upwardly from the valleys 24. Without being bound by theory, it is believed the cones 22 extended upwardly as described and depicted herein impart perceivable softness, a relatively less plastic feel and overall comfort to the skin when a film layer from which the cones 22 extend is the skin-facing layer in absorbent articles. The upwardly-projecting cones 22 reduce contact surface area between the film layer 21 and the wearer/user's skin. The cones 22 also provide visibly perceivable texture to the upper side 16 of the laminate web 10, reducing gloss or a shiny appearance that the film may otherwise present. Additionally, by reducing contact surface area between the wearer/user's skin and a topsheet for an absorbent article, formed of the laminate contemplated herein, the cones greatly reduce the potential for sticking of the topsheet the wearer/users skin, following a discharge of fluid to the article.

In examples in which the cones 22 have open ends and define apertures 25, the cones may be formed by applying high pressure vacuum to the inner or lower surface of a forming screen having an outside or upper forming surface of the precursor web is drawn against. Such methods of aperturing are sometimes known as "vacuum forming" and are described in greater detail in, for example, U.S. Pat. Nos. 4,463,045 and 4,552,709. Examples of alternative mechanical deformation are disclosed in U.S. Pat. Nos. 4,798,604; 4,780,352; 3,566,726; 4,634,440; WO 97/40793, and European Patent EP 525,676.

For examples of laminate webs contemplated herein, it is preferred that the cones 22 be created in the film to have an average height ch (see FIG. 1), from the lowest portions of their surrounding valleys 24, of 100 μm to 500 μm, for purposes of soft, cloth-like skin feel and resistance to sticking. For purposes of providing for suitable softness, appearance, skin feel, resistance to sticking and fluid acquisition capability, is preferred that the apertures delineated by the cones have an average numerical density 140 to 760, more preferably 240 to 650, and even more preferably 300 to 590 apertures per $cm^2$ x-y planar surface area in z-direction plan view of the upper surface the film. For purposes of providing suitable fluid acquisition capability, it is preferred that the apertures have an average largest x-y plane dimension ar (see FIG. 2A) of 150 μm to 500 μm, across the open region of the aperture, between opposing circumscribing rims or side walls of the cone.

(For purposes herein, only apertures that are entirely circumscribed by and appear entirely within the outer perimeter of the sample measurement area, are counted, in determining numerical density and average largest x-y dimension (i.e., apertures that straddle the outer perimeter of the sample measurement area are not counted.) Counts of numerical density, and measurements of cone height and x-y aperture dimensions may be made using any suitable method, and may be facilitated using magnified scale photography (such as SEM photography) and image analysis software. For purposes herein the sample measurement area may be any 0.25 cm², square, x-y planar area at any location of the subject topsheet film layer having cones formed therein.)

Apparatus and Method for Manufacturing Laminate Web

The cones 22 in web 10 can be formed using any processes known in the art including but not limited to those described in references cited above.

Non-limiting examples of methods for vacuum formation and mechanical deformation are described in references cited above. With respect to ultrasonics, additional methods are disclosed in U.S. Pat. Nos. 5,269,981 and 5,269,981.

Forming rolls for a vacuum or mechanical deformation process for forming cones 22 are typically generally cylindrical. The rolls can be made from any suitable materials including, but not limited to steel, aluminum or plastic. The steel may be made of corrosion resistant and wear resistant steel, such as stainless steel. At least one of the rolls may be heated. Alternatively, it may be desired that the forming roll over which the precursor laminate is drawn be cooled, to speed the process by decreasing the time needed for the laminate layers 20, 21 to fully solidify and become stable.

A laminate of one example contemplated herein may be produced by applying a precursor nonwoven web (layer) to a precursor polymer film layer to obtain a precursor laminate web, and, subsequently, forming the cones 22 in the polymer film layer. The precursor nonwoven web layer may be bonded to the precursor film layer to form the precursor laminate by any suitable mechanism, including but not limited to thermal bonding in a pattern of spot bonds, adhesive bonding and fusion bonding.

In examples in which the polymer constituent(s) of the precursor film layer and of the fibers of the precursor nonwoven layer are formed of compatible polymers, the fibers of the nonwoven web layer contacting the film layer may be caused to be fusion-bonded at random locations at which fibers directly contact the film layer, for example, as disclosed in pending U.S. application Ser. No. 16/554,948. An example of such a fiber-to-film fusion bond 41 may be seen in FIG. 3C. In particular examples, both the sheath components of bicomponent nonwoven fibers, and the film, may each be, respectively, formed of compatible polymers (e.g., both may be formed of polyethylene, in some examples), such that when fibers of the precursor nonwoven web are brought into contact with the precursor film in a semi-molten state promptly following extrusion, heat energy still residing in the extruded precursor film may be sufficient to transfer to and partially melt the fiber sheath components, such that randomly-disposed fusion bonds will form between the fiber sheaths and the film where the fibers are brought into contact with the film.

Alternatively, a laminate web contemplated herein may be produced by laminating a precursor nonwoven web layer and a precursor polymer film already imparted with a pattern of cones 22. The precursor nonwoven web layer and the polymer film may be provided either directly from their respective web making processes or indirectly from supply rolls and moved in the machine direction to the laminating process.

Figure 5:
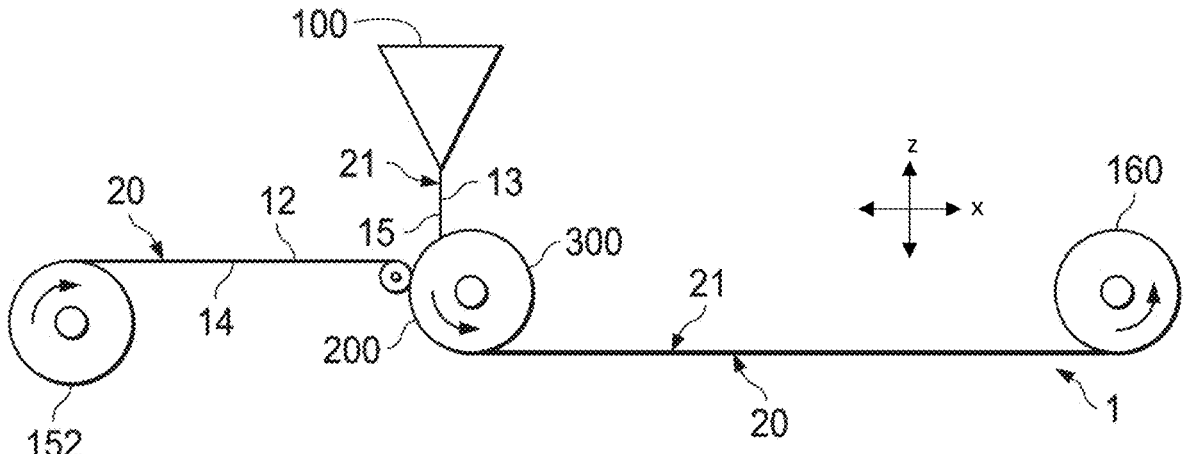
FIG. 5 is a schematic representation of a process for forming a laminate web as contemplated herein.

Referring to FIG. 5, an example of a process for producing examples of laminate webs 10 contemplated herein may include a step of laminating a nonwoven layer 20 and a polymer film layer 21 and a subsequent step of forming a pattern of cones via a cone forming unit 200. Cone forming unit 200 may be a vacuum forming roller with an outer cylindrical forming surface formed with a pattern of holes therein, reflecting the pattern, shape, size and numerical density of cones desired to be imparted to the film. Generally, the configuration of the pattern of holes on the forming roller may be adjusted to impart the desired features to the cones, along with other process variables including film composition, basis weight and temperature, throughput speed, etc. As noted above, the forming roller may be controllably cooled for additional control over the process. Vacuum may be drawn from inside the roller, creating a pressure differential between the inside and outside of the roller, which draws the film into the holes to form cones that approximately reflect the shapes of the holes and walls thereof, which with suitable control can be caused to rupture and thereby form apertures through the film.

In another example of a process, a precursor film layer component may be produced in line, and deformed to have imparted a pattern of cones and apertures, prior to being laminated with a precursor nonwoven web. The precursor film layer with cones may be laminated with precursor nonwoven web using adhesive or thermal spot bonding processes, to form laminate web 10.

Application of Laminate Web

Laminate webs contemplated herein can be used to make components of disposable absorbent articles such as but not limited to incontinence pads and pants, diapers, training pants, feminine hygiene pads/sanitary napkins and disposable menstrual pants.

The web contemplated herein is preferably used as a topsheet for an absorbent article. In some examples, the upper side of the web 10 having a pattern of upwardly-projecting cones is in contact with the skin.

Absorbent Article

An absorbent article contemplated herein may include a topsheet and a backsheet joined to the topsheet, wherein the topsheet is formed of a laminate web as contemplated herein. It may further include an absorbent structure between the topsheet and the backsheet. The absorbent article may be produced industrially by any suitable means. The different layers may be assembled using standard conventional processes such as embossing, thermal bonding, or gluing or combination of both.

Topsheet

A surface of the web having a plurality discrete extended elements is preferably, disposed on a side in contact with the skin.

Backsheet

Any conventional backsheet materials commonly used for absorbent articles may be used as backsheet. In some embodiments, the backsheet may be impervious to malodorous gases generated by absorbed bodily discharges, so that the malodors do not escape. The backsheet may or may not be breathable.

Absorbent Structure

It may be desirable that the article further include an absorbent structure disposed between the topsheet and the backsheet. As used herein, the term "absorbent structure" refers to a material or combination of materials suitable for absorbing, distributing, and storing fluids such as urine, blood, menses, and other body exudates. Any conventional materials for absorbent structure suitable for absorbent articles may be used as absorbent structure.

Fiber-Fiber Distance Measurement

Z-direction distances between individual fibers in a non-woven layer in a laminate sample having a film layer and a nonwoven layer is measured using micro-CT fiber-to-fiber distance measurement based on analysis of a 3D x-ray image of a sample obtained on a micro-CT instrument having a cone beam microtomograph with a shielded cabinet such as Scanco μCT 50 (Scanco Medical AG, Switzerland) and equivalents. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. Multiple individual projection images of the sample, generated as it is rotated, are collected and then recon-structed into a single 3D image. The instrument is interfaced with a computer running software to control the image acquisition and reconstruction of the raw data into a 3D image. The 3D image is then analyzed using image analysis software such as MATLAB (The Mathworks, Inc., MA, USA) and Avizo Lite (Visualization Sciences Group/FEI Company, MA, USA) and equivalents to identify and seg-ment out the film layer from the nonwoven layer, and measure Z-direction distances between individual fibers in the nonwoven portion of the laminate sample.

Sample Preparation:

To obtain a sample for measurement, lay a film-nonwoven laminate out flat and die cut a circular piece with a diameter of 7 mm. If the laminate is a component of an absorbent article, tape the absorbent article to a rigid flat surface in a planar configuration, and carefully separate the laminate from the other components of the absorbent article. A scalpel and/or cryogenic spray such as Cyto-Freeze (Control Com-pany, TX, USA) can be used to remove the laminate from the other components of the absorbent article, if necessary, to avoid extension of the laminate. Once the laminate has been removed from the article, proceed with die cutting the sample as described above.

A sample may be cut from any location containing the laminate to be analyzed. When selecting a location for sampling, care should be taken to avoid embossed regions, if any, in the absorbent article where the laminate may have been crushed and/or compressed during the article making process, as well as any folds, wrinkles or tears.

Image Acquisition:

The micro-CT instrument is set up and calibrated accord-ing to the manufacturer's specifications. The sample is placed into an appropriate holder, between two rings of a low density material, such as foam, which have an inner diameter of at least 4 mm. This allows the central region of the sample to lay horizontal and be scanned without having any other materials directly adjacent to its upper and lower surfaces. Analysis is performed within this central region. A single 3D dataset of contiguous 3 μm isotropic voxels is collected. The 3D dataset is centered on the central analysis region, having dimensions of 7 mm on each side in the XY-plane and a sufficient number of slices to fully include the Z-direction of the sample. Images are acquired with the source at 45 kVp and 88 μA with no additional low energy filter. Current and voltage settings may be optimized to produce the maximum contrast in the projection data with sufficient x-ray penetration through the sample, but once optimized held constant for all substantially similar samples.

A total of 3200 projection images are obtained with an integration time of 1000 ms and 3 averages. The projection images are reconstructed using acquisition and reconstruc-tion software accompanies the instrument into a 3D dataset having an isotropic spatial resolution of 3 μm, and saved in 16-bit RAW format to preserve the full detector output signal for analysis.

Image Processing:

The 3D dataset is loaded into the image analysis software, and trimmed to a rectangular prism 3D image of the analysis region by removing the surrounding holder and the low density mounting material from the 3D dataset. Trimming is performed such that the maximum amount of the sample in the analysis region is retained in the 3D image, and the empty space above and below the sample is minimized. The trimmed 3D image is scaled from 16-bit to 8-bit for the purpose of convenience in data analysis, and thresholded using Otsu's method which calculates the threshold level that minimizes the weighted intra-class variance, to separate and remove the background signal due to air, but maintain the signal from the film and fibers within the sample image. Film and/or fiber containing voxels are referred to as "mate-rial" voxels.

A connected components algorithm is executed on the trimmed 3D image, which identifies and groups together any material voxels that are 26-connected (touching one of their faces, edges, or corners) to any neighboring material voxels. Any material voxel clusters containing fewer than 1000 connected voxels are identified as noise and removed from the 3D image.

The 3D image is oriented so that the film upper surface is as close to parallel with the XY-plane as possible.

The film layer is identified and distinguished from non-woven fibers using a Z-direction vector, such that given an XY-plane position, a typical Z-direction vector traveling from the top of the 3D image to the bottom will first pass through the film, and then pass through underlying nonwo-ven fibers. However, in the regions where apertures formed in the film layer, a fiber may be the first material encoun-tered, and must be distinguished from the film layer. As an individual Z-direction vector travels from the top of the 3D image downward, there may be a series of contiguous material voxels in the vector as it passes through the first material encountered. The last material voxel in this series of contiguous material voxels is identified as a potential lower film surface or "bottom of film" voxel. This process is repeated as a Z-direction vector is passed through every XY-plane position in the 3D image, and all of the potential bottom of film voxels are identified. A connected compo-nents algorithm is once again executed on only the identified potential bottom of film voxels in the 3D image, which groups together potential bottom film voxels that are 26-con-nected (touching one of their faces, edges, or corners) to neighboring potential bottom of film voxels. The lower surface of the film is identified as the single largest continu-ous cluster of potential bottom of film voxels.

The fiber-to-fiber distance is measured along the Z-direc-tion vectors, below the identified lower surface of the film layer from where one fiber ends to the beginning of the next underlying fiber. If no film voxel was identified in the Z-direction vector, due to a hole or aperture in the film layer, any distance measurements from that vector are ignored. Any Z-direction vectors which do not encounter any fibers are also ignored. The median fiber-to-fiber distance of all the distance measurements in the 3D image is calculated and recorded to the nearest 0.1 μm. A total of three substantially similar replicate film-nonwoven laminate samples are analyzed in like manner, and the average of the three recorded median fiber-to-fiber distances is reported to the nearest 0.1 μm.

In view of the foregoing disclosure, the following non-limiting examples are contemplated:

1. An absorbent personal hygiene article comprising a topsheet, the topsheet comprising a laminate web (10) comprising an upper layer of polymer film (21) directly bonded to a lower layer of nonwoven web (20); wherein the polymer film (21):

comprises predominantly polyethylene (PE), preferably a homogeneous blend of LDPE and LLDPE, and more preferably a homogeneous blend of at least 50% by weight LDPE, and LLDPE;

has a basis weight of 8 gsm to 20 gsm and more preferably 10 gsm to 15 gsm;

has formed thereon a pattern of cones (22) and valleys (24), the cones projecting upwardly from adjacent valleys to rim edges (23) proximate an upper side (16) of the laminate web (10), the cones circumscribing and defining apertures (25) through the polymer film (21), wherein the nonwoven web has a basis weight of 12 gsm to 24 gsm, more preferably 12 to 18 gsm, and even more preferably 14 gsm to 16 gsm, and comprises staple fibers with randomly-distributed fiber-to-fiber fusion bonds thereamong, wherein the randomly-distributed fusion bonds are not compression bonds, and wherein the staple fibers:

have an average denier of 3-12, more preferably 5-9, and even more preferably 5-7; and are spun of one or more polyolefins;

wherein each of the film and the staple fibers have been modified with one or more hydrophilizing agents.

2. The absorbent article of example 1 wherein the apertures have an average largest x-y dimension (ar) of 150 μm to 500 μm.

3. The absorbent article of either of examples 1 or 2 wherein the cones have an average height (ch) of 100 μm to 500 μm.

4. The absorbent article of any of the preceding examples wherein the apertures have a numerical density of 140 to 760, more preferably 240 to 650, and even more preferably 300 to 590, apertures per $cm^2$ x-y plane surface area of the laminate web.

5. The absorbent article of any of the preceding examples, wherein the polymer film comprises no more than 10%, more preferably no more than 5%, and even more preferably less no more than 1%, by weight, HDPE, polypropylene or PET.

6. The absorbent article of any of the preceding examples, wherein the staple fibers comprise bicomponent fibers.

7. The absorbent article of example 6, wherein the bicomponent fibers have a sheath-core configuration, wherein the sheath component comprises one or more polyolefins.

8. The absorbent article of example 7 wherein the sheath component comprises a polyolefin selected from the group consisting of polyethylene, polypropylene, and combinations thereof.

9. The absorbent article of example 7 wherein the sheath component comprises polyethylene.

10. The absorbent article of any of examples 7-9 wherein the core component comprises PET.

11. The absorbent article of any of examples 6-10 wherein the two components of the bicomponent fibers are present in a weight ratio of 40:60 to 60:40, more preferably 45:55 to 55:45.

12. The absorbent article of any of the preceding examples wherein the film has been surface treated with a hydrophilizing agent.

13. The absorbent article of any the preceding examples wherein the film has been formed from a resin having a hydrophilizing agent blended thereinto.

14. The absorbent article of any of the preceding examples wherein the fibers have been surface-treated with a hydrophilizing agent.

15. The absorbent article of any of the preceding examples wherein polymer component(s) of the fibers have had a hydrophilizing agent blended thereinto.

16. The absorbent article of any of the preceding examples wherein the fibers comprise polyethylene and are partially fusion-bonded to the film.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments contemplated herein have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An absorbent personal hygiene article comprising a topsheet, the topsheet comprising a laminate web comprising an upper layer of polymer film directly bonded to a lower layer of nonwoven web;

wherein the polymer film:

comprises predominantly polyethylene (PE);

has a basis weight of 8 gsm to 20 gsm;

has formed thereon a pattern of cones and valleys, the cones projecting upwardly from adjacent valleys to rim edges proximate an upper side of the laminate web, the cones circumscribing and defining apertures through the polymer film, wherein the nonwoven web has a basis weight of 12 gsm to 24 gsm, and comprises staple fibers with randomly-distributed fiber-to-fiber fusion bonds thereamong, wherein the randomly-distributed fusion bonds are not compression bonds, and wherein the staple fibers:

have an average denier of 3-12; and are spun of one or more polyolefins;

wherein each of the film and the staple fibers have been modified with one or more hydrophilizing agents.

2. The absorbent article of claim 1 wherein the apertures have an average largest x-y dimension of 150 µm to 500 µm.

3. The absorbent article of claim 1 wherein the cones have an average height of 100 µm to 500 µm.

4. The absorbent article of claim 1 wherein the apertures have a numerical density of 140 to 760 apertures per cm² x-y plane surface area of the laminate web.

5. The absorbent article of claim 1, wherein the polymer film comprises no more than 10% by weight, HDPE, polypropylene or PET.

6. The absorbent article of claim 1, wherein the staple fibers comprise bicomponent fibers.

7. The absorbent article of claim 6, wherein the bicomponent fibers have a sheath-core configuration, wherein the sheath component comprises one or more polyolefins.

8. The absorbent article of claim 7 wherein the sheath component comprises a polyolefin selected from the group consisting of polyethylene, polypropylene, and combinations thereof.

9. The absorbent article of claim 7 wherein the sheath component comprises polyethylene.

10. The absorbent article of claim 9 wherein the core component comprises PET.

11. The absorbent article of claim 10 wherein the two components of the bicomponent fibers are present in a weight ratio of 40:60 to 60:40.

12. The absorbent article of claim 1 wherein the film has been surface treated with a hydrophilizing agent.

13. The absorbent article of claim 1 wherein the film has been formed from a resin having a hydrophilizing agent blended thereinto.

14. The absorbent article of claim 1 wherein the fibers have been surface-treated with a hydrophilizing agent.

15. The absorbent article of claim 1 wherein polymer component(s) of the fibers have had a hydrophilizing agent blended thereinto.

16. The absorbent article of claim 1 wherein the fibers comprise polyethylene and are partially fusion-bonded to the film.

17. An absorbent personal hygiene article comprising a topsheet, the topsheet comprising a laminate web comprising a polymer film directly bonded to a nonwoven web;

the polymer film comprising predominantly polyethylene (PE), the polymer film comprising a pattern of cones and valleys, the cones projecting upwardly from adjacent valleys to rim edges proximate an upper side of the laminate web, the cones circumscribing and defining apertures through the polymer film, the nonwoven web comprising staple fibers having randomly-distributed fiber-to-fiber fusion bonds formed without z-direction compression, the staple fibers comprising one or more polyolefins.

18. The absorbent article of claim 1, wherein each of the film and the staple fibers have been modified with one or more hydrophilizing agents.

19. The absorbent article of claim 1, wherein the apertures of the polymer film have an average numerical density of 300 to 590 apertures per cm² x-y planar surface area.

20. The absorbent article of claim 1, wherein the staple fibers of the nonwoven web comprise bicomponent fibers having a sheath-core configuration, wherein the sheath component comprises one or more polyolefins, and the core component comprises polyethylene terephthalate (PET).

* * * * *